United States Patent
Tsuzuki et al.

(10) Patent No.: US 6,417,144 B2
(45) Date of Patent: Jul. 9, 2002

(54) SOLUTION FOR CONTACT LENSES

(75) Inventors: Akira Tsuzuki; Sadayasu Tanikawa, both of Aichi (JP)

(73) Assignee: Menicon., Ltd., Nagoya (JP)

( * ) Notice: Subject to any disclaimer, the term of this patent is extended or adjusted under 35 U.S.C. 154(b) by 0 days.

(21) Appl. No.: 09/879,050

(22) Filed: Jun. 13, 2001

(30) Foreign Application Priority Data

Jun. 14, 2000 (JP) .................................. 2000-177730

(51) Int. Cl.⁷ ............................. C11D 1/42; C11D 1/72; C11D 1/94
(52) U.S. Cl. ....................... 510/115; 510/422; 510/499; 510/506; 422/28
(58) Field of Search ................. 510/115, 499, 510/422, 506; 422/28

(56) References Cited

U.S. PATENT DOCUMENTS

| | | | | |
|---|---|---|---|---|
| 4,285,738 A | * | 8/1981 | Ogata ........................ 134/26 |
| 4,370,174 A | * | 1/1983 | Braithwaite, Jr. ............ 134/7 |
| 4,832,754 A | * | 5/1989 | Trumpower .................. 134/30 |
| 4,908,147 A | | 3/1990 | Tsao et al. | |
| 5,281,277 A | * | 1/1994 | Nakagawa et al. ........... 134/18 |
| 5,330,752 A | * | 7/1994 | Park et al. .................. 424/94.4 |
| 5,574,050 A | * | 11/1996 | Carrell et al. ............... 514/357 |
| 5,703,024 A | * | 12/1997 | Park et al. .................. 510/100 |
| 5,840,250 A | * | 11/1998 | Park et al. .................. 422/28 |
| 6,008,170 A | * | 12/1999 | Tanaka et al. ............... 510/114 |

FOREIGN PATENT DOCUMENTS

| | | |
|---|---|---|
| DE | 31 34 723 A | 4/1982 |
| DE | 0 233 842 A | 8/1987 |
| JP | 76005413 | * 2/1976 |
| JP | 57-165305 | * 10/1982 |
| JP | 08183705 | * 7/1996 |
| WO | WO 94/19027 | 9/1994 |

OTHER PUBLICATIONS

Derwent Abstracts, Accession Number XP-002178547, JP 03 068503, Mar. 25, 1991.

* cited by examiner

*Primary Examiner*—Gregory Delcotto
(74) *Attorney, Agent, or Firm*—Oblon, Spivak, McClelland, Maier & Neustadt, P.C.

(57) ABSTRACT

A solution for contact lenses which comprises an amino acid type cationic surfactant and at least one nonionic surfactant.

5 Claims, 1 Drawing Sheet

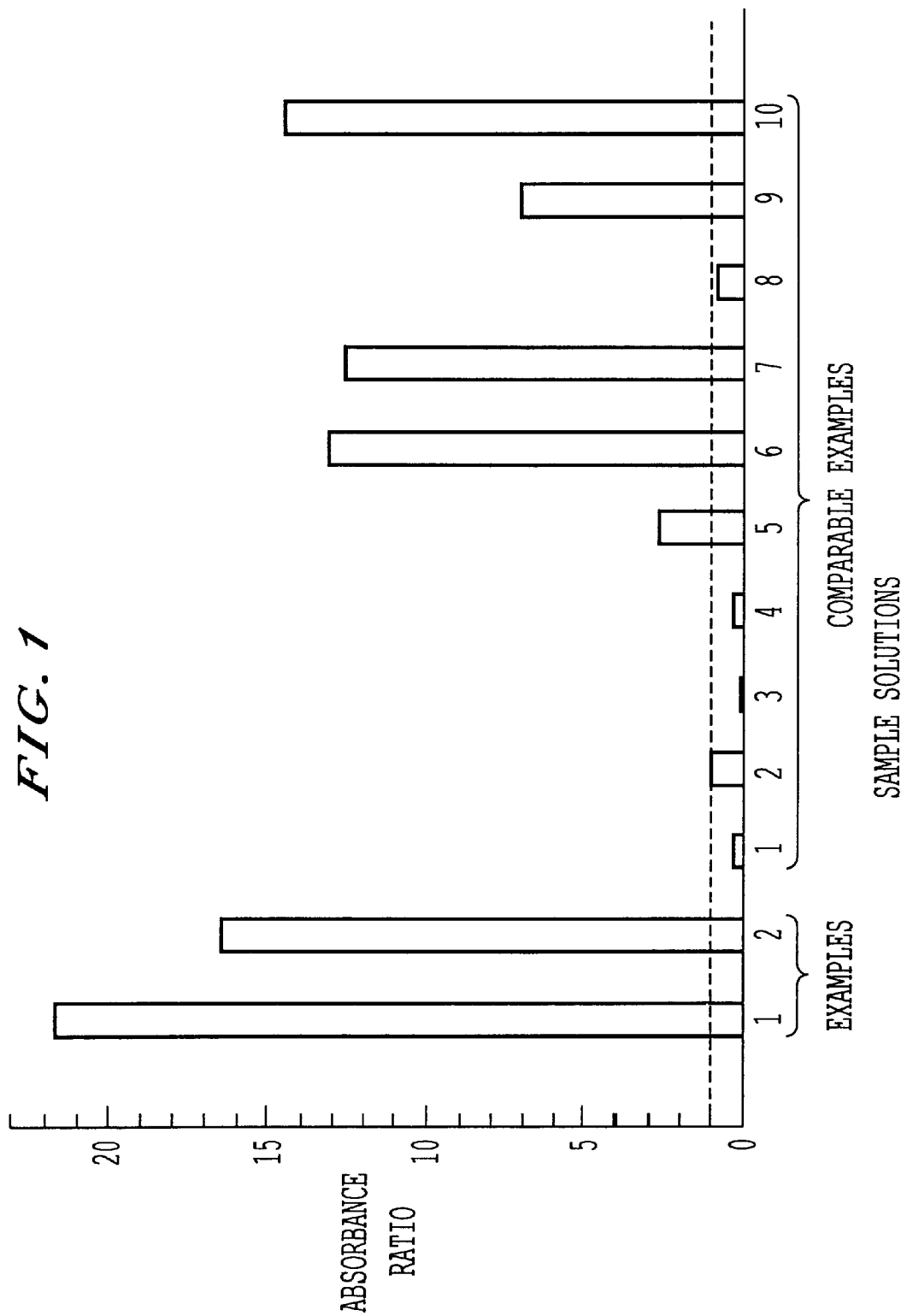

SOLUTION FOR CONTACT LENSES

The present invention relates to a solution for contact lenses, particularly a solution for contact lenses having an excellent cleaning effect and having an adequate safety for the eye.

Conventionally, contact lenses have been classified into water-nonabsorptive contact lenses and water-absorptive contact lenses, and classified into hard contact lenses and soft contact lenses. On each of these contact lenses, a stain of e.g. lipids (eye lipids) derived from the tear may be deposited when the lens is put on the eye in some cases, and such a stain on the lens due to the tear may cause deterioration in comfortableness in wearing or eye problems such as failure of eyesight or congestion of cornea, and accordingly it is essential to apply a cleaning treatment to a contact lens in order to safely and comfortably use the contact lens every day.

For such a cleaning treatment of a contact lens, a proper solution for contact lenses having a cleaning or removing effect over a stain is usually used. As such a solution for contact lenses, various solutions having a surfactant as a cleaning component added and incorporated therein have been proposed, and one having a nonionic surfactant such as a polyoxyalkylene block copolymer such as a polyoxyethylene-polyoxypropylene block copolymer or a derivative thereof incorporated may, for example, be known.

However, with respect to the cleaning solution for contact lenses containing such a nonionic surfactant, importance is usually attached to safety for the eye, and the concentration of the surfactant in the solution is suppressed to be as low as possible. Accordingly, with a conventional cleaning solution for contact lenses containing such a surfactant at a low concentration, no adequate cleaning power such as lipid-solubilizing power may be obtained. Accordingly, there is a fear that when a cleaning treatment of a contact lens is carried out by using such a cleaning solution, a stain of e.g. lipids tends to remain and be accumulated on the contact lens, and the eye may harmfully be influenced.

On the other hand, surfactants are classified into cationic surfactants, anionic surfactants, nonionic surfactants and ampholytic surfactants depending upon their dissociation state in their aqueous solutions. Among them, various surfactants which are classified into cationic surfactants, particularly surfactants which consist of an amino acid derivative, i.e. amino acid type cationic surfactants, have conventionally been proposed as disinfectant cleaning agents or compositions for disinfection.

For example, JP-B-51-5413 proposes a disinfectant cleaning agent to be used for disinfection and sterilization e.g. in a food sanitation field, in a field of environmental public health, in an industrial field, or in a field of agriculture and horticulture, characterized by containing, as the main component, one or at least two of amino acid type cationic surfactants having a certain structural formula. Further, JP-A-57-165305 proposes a method of blending Nα-cocoyl-L-arginine ethyl ester·DL-pyrrolidone carboxylate which is an amino acid type cationic surfactant in a certain proportion with another surfactant type sterilizer such as a salt of chlorhexidine or benzalkonium chloride, so as to reinforce the effectiveness of said surfactant type sterilizer and make it possible to use the sterilizer as a sterilizer for medical use. Further, JP-A-8-183705 proposes a composition for sterilization having a strong disinfection power and being low irritative to the skin or mucous membrane, which comprises a sterilizer such as benzalkonium chloride or benzethonium chloride and Nα-long chain acylarginine branched alkyl ester or its salt which is an amino acid type cationic surfactant blended, and the composition is considered to be suitable for sterilization of the skin, oral cavity and contact lenses.

As mentioned above, the amino acid type cationic surfactant is well known as a sterilization component among cationic surfactants, and in addition, it is considered to have a cleaning effect as a common property of a surfactant, since it is one type of surfactants. However, its cleaning effect, particularly an effect or performance obtainable when it is applied to contact lenses has not been well clarified so far.

Under these circumstances, the present inventors have conducted extensive studies and as a result, found that when an amino acid type cationic surfactant and a nonionic surfactant are used together, lipid-solubilizing powers of the respective surfactants are greatly improved mutually without impairing contact lenses as compared with a case where each surfactant is used alone, and that with a solution comprising an amino acid type cationic surfactant and at least one nonionic surfactant, a useful cleaning effect over a stain of lipids on a contact lens and a decrease in toxicity against the eye can be achieved simultaneously.

The present invention has been accomplished on the basis of the above discoveries, and it is an object of the present invention to provide a solution for contact lenses which is excellent in cleaning effect over a stain on a contact lens, particularly a stain of lipids without impairing the contact lens, and which secures adequate safety for the eye.

According to the present invention, there is provided a solution for contact lenses which comprises an amino acid type cationic surfactant and at least one nonionic surfactant.

Now, the present invention will be described in detail with reference to the preferred embodiments.

In the accompanying drawing:

FIG. 1 is a bar graph illustrating absorbance ratios of sample solutions obtained in Examples.

In the solution for contact lenses according to the present invention, as cleaning components, an amino acid type cationic surfactant and at least one nonionic surfactant are combined and incorporated as essential components, and lipid-solubilizing powers of the respective surfactants are synergistically improved. Accordingly, by appropriately adjusting the concentrations of the amino acid type cationic surfactant and the nonionic surfactant, a cleaning or removal effect over a stain on a contact lens, particularly a stain due to the tear attached to a contact lens, particularly a stain of lipids, can advantageously be realized, while securing adequate safety for the eye and without impairing the contact lens.

In a preferred embodiment of the solution for contact lenses according to the present invention, as the amino acid type cationic surfactant, N-coconut oil fatty acid acyl L-arginine ethyl·DL-pyrrolidone carboxylate is advantageously used.

In another preferred embodiment of the present invention, as the nonionic surfactant, a polyoxyethylene-polyoxypropylene block copolymer or its derivative is advantageously used.

In the solution for contact lenses according to the present invention, the amino acid type cationic surfactant is contained preferably in a proportion of from 0.001 to 1.0% (w/v), and the nonionic surfactant is contained preferably in a proportion of from 0.1 to 3.0% (w/v). By employing such contents, safety for the eye can advantageously be secured, and the cleaning effect over a stain of lipid can more advantageously be obtained.

Further, in the solution for contact lenses according to the present invention, an ampholytic surfactant may further be incorporated in addition to the amino acid type cationic surfactant and the nonionic surfactant.

Further, the solution for contact lenses according to the present invention may further contain, in addition to the amino acid type cationic surfactant and the nonionic surfactant, at least one member selected from the group consisting of a disinfectant, a thickener, a buffering agent, a chelating agent, an isotonicity agent, and a cationic surfactant other than the amino acid type cationic surfactant or an anionic surfactant, and by addition of such an additive component, a further function depending upon the component may advantageously be imparted.

Further, the solution for contact lenses of the present invention has an adequate safety for the eye and can thereby be used as eye drops, and it may be administered to the eye having a contact lens put thereon so as to bring the solution into contact with the lens to clean the lens put on the eye.

Here, in the solution for contact lenses of the present invention, the amino acid type cationic surfactant which is one essential component consists of an amino acid derivative, as is well known. It shows a sterilization effect as usual, and in the present invention, it is used as a component to increase the cleaning power (such as power for solubilizing fat such as lipids and protein) by using it together with a nonionic surfactant.

In the present invention, as the amino acid type cationic surfactant, an ophthalmologically acceptable cationic surfactant consisting of an amino acid derivative, containing a $C_{8-18}$ alkyl group, such as alkyldiaminoethyl glycine or dialkylaminoethyl glycine, is advantageously employed, and among such amino acid type cationic surfactants, particularly preferably N-coconut oil fatty acid acyl L-arginine ethyl·DL-pyrrolidone carboxylate is suitably used. As this compound, one having an amino group bonded to an α-carbon in L-arginine ethyl ester acylated by a coconut oil fatty acid residue, and having DL-pyrrolidone carboxylic acid added thereto, may be mentioned.

The amino acid type cationic surfactant is contained usually in a proportion of from 0.001 to 1.0% (w/v) in the solution for contact lenses of the present invention. If the concentration of the amino acid type cationic surfactant is lower than 0.001% (w/v), the cleaning power such as lipid-solubilizing power tends to hardly be improved synergistically even if the nonionic surfactant as mentioned hereinafter is used together, and if it is higher than 1.0% (w/v), the shape or physical properties of a contact lens may be impaired, such that the base curve of a contact lens may be changed.

Further, in the solution for contact lenses of the present invention, a nonionic surfactant is also one essential component, and the nonionic surfactant may, for example, be a polyoxyethylene-polyoxypropylene block copolymer or its derivative, which has a polyoxyethylene (POE) chain composed of a polyoxyethylene group and a polyoxypropylene (POP) chain composed of a polyoxypropylene group, a POE alkyl ether, a POE alkyl phenyl ether, a polyoxyethylene sorbitan alkyl ester, a polyoxyethylene hardened castor oil, a fatty acid monoglyceride, a propylene glycol fatty acid ester, a fatty acid sucrose ester or a (POE)-(POP) ethylenediamine condensate (poloxamine). Preferred is a polyoxyethylene-polyoxypropylene block copolymer or its derivative.

Here, as the polyoxyethylene-polyoxypropylene block copolymer, Pluronic, Pluronic R, Tetronic, Tetronic R and Poloxamer (manufactured by BASF) may, for example, be employed, and among them, use of e.g. Poloxamer 124, Poloxamer 188, Poloxamer 237, Poloxamer 338 or Poloxamer 407 may be recommended.

As a specific example of the derivative of the polyoxyethylene-polyoxypropylene block copolymer, a high-molecular compound obtained by etherification or esterification of a hydroxyl group on one or each terminal of a polyoxyethylene-polyoxypropylene block copolymer by a conventional modification means may be mentioned, and its representative examples include POE-POP type ones such as polyoxyethylene-polyoxypropylene mono/dialkyl ether and polyoxyethylene-polyoxypropylene mono/dialkyl ester, and POE-POP-POE type ones.

Here, among such polyoxyethylene-polyoxypropylene block copolymer derivatives, the POE-POP type one may be represented by any of the following general formulae (a) to (h).

(a) RO—(OE)$_x$—(OP)$_y$—H
(b) HO—(OE)$_x$—(OP)$_y$—R
(c) RCOO—(OE)$_x$—(OP)$_y$—H
(d) HO—(OE)$_x$—(OP)$_y$—COR
(e) RO—(OE)$_x$—(OP)$_y$—R'
(f) RO—(OE)$_x$—(OP)$_y$—COR'
(g) RCOO—(OE)$_x$—(OP)$_y$—R'
(h) RCOO—(OE)$_x$—(OP)$_y$—COR'

In the above general formulae (a) to (h), OE is an oxyethylene group ($CH_2CH_2O$), OP is an oxypropylene group ($CH_2CH(CH3)O$), and each of R and R' is a $C_{1-3}$ linear or branched alkyl group, and in the general formulae (e) to (h), R and R' may be the same or different. Further, x and y which are numbers of repetitions of the above OE and OP, are integers of from 5 to 100 and from 1 to 10, respectively.

Specific examples of the polyoxyethylene-polyoxypropylene block copolymer derivatives represented by the above general formulae (a) to (h) include POE(10) POP(4) monocetyl ether, POE(20)POP(4) monocetyl ether, POE(20)POP(8) monocetyl ether, POE(20)POP(6) decyl tetradecyl ether, POE(30)POP(6) decyl tetradecyl ether, POE(10)POP(4) monocetyl ester, POE(20)POP(4) monocetyl ester, POE(20)POP(8) monocetyl ester, POE(20)POP (6) decyl tetradecyl ester, POE(30)POP(6) decyl tetradecyl ester, POE(10)POP(4) monolauryl ether, POE(10)POP(4) monolauryl ester, POE(3)POP(1) cetyl acetate, POE(3)POP (1) isocetyl acetate, POE(3)POP(1) cetyl acetate and POE (3)POP(1) isocetyl acetate.

Further, examples of the POE-POP-POE type high-molecular compounds as representative examples of the polyoxyethylene-polyoxypropylene block copolymer derivatives, include compounds represented by the following general formulae (i) to (1).

(i) RO—(OE)$_a$—(OP)$_b$—(OE)$_a$—H
(j) RO—(OE)$_a$—OP)$_b$—(OE)$_a$—R'
(k) RCOO—(OE)$_a$—(OP)$_b$—(OE)$_a$—H
(l) RCOO—(OE)$_a$—(OP)$_b$—(OE)$_a$—COR'

In the above general formulae (i) to (1), each of OE, OP, R and R' is as defined for the above general formulae (a) to (h), and aand bwhich are numbers of repetitions of OE and OP, are integers of from 5 to 150 and from 10 to 100, respectively, and a preferred combination is (a,b)=(12,20), (80,27), (64,37), (141,44) or (101,56).

Here, the nonionic surfactant is contained usually in a proportion of from 0.1 to 3.0% (w/v) in the solution for contact lenses of the present invention. If the concentration of the nonionic surfactant is lower than 0.1% (w/v), the cleaning power such as lipid-solubilizing power tends to hardly be improved synergistically even if it is used together with the above-mentioned amino acid type cationic surfactant. On the other hand, if it is higher than 3.0% (w/v), the lens may be impaired, or the safety may decrease such that the eye mucous membrane may be irritated.

With respect to the solution for contact lenses comprising such a nonionic surfactant and the above amino acid type cationic surfactant, the cleaning power, particularly lipid-solubilizing power, based on the surfactant properties of the amino acid type cationic surfactant and the nonionic surfactant can synergistically be improved, whereby an adequate cleaning effect can be obtained with low concentrations of the amino acid type cationic surfactant and the nonionic surfactant.

The solution for contact lenses of the present invention is prepared by adding and incorporating such specific two types of surfactants in proper amounts into a proper aqueous medium in an optional order in a conventional method. In the present invention, in addition to the specific surfactants, one or more additive components conventionally used for solutions for contact lenses may further be incorporated in a conventional amount as the case requires. Such an additive component is preferably one which has a high safety for the body, which is adequately acceptable ophthalmologically, and which has no influence over the shape or physical properties of a contact lens, and used preferably in an amount satisfying such essentialities, whereby a function depending upon the additive component can advantageously be imparted to the solution for contact lenses of the present invention without impairing the effects of the present invention.

In the solution for contact lenses of the present invention, a known surfactant, specifically an ampholytic surfactant, a cationic surfactant other than the amino acid type cationic surfactant, or an anionic surfactant may, for example, be added and incorporated so long as it does not inhibit the synergistic effect obtained by combination of the amino acid type cationic surfactant with the nonionic surfactant, in an amount which does not impair the effect. Here, the ampholytic surfactant may, for example, be an amine oxide such as alkyldimethylamine oxide; a betain such as alkyldimethylamino fatty acid betain or alkylcarboxymethylhydroxyethyl imidazolium; an amino acid type ampholytic surfactant; or an arginine type ampholytic surfactant, and preferred is an arginine type ampholytic surfactant from such a reason that the eye will be less irritated and the safety is high, and particularly preferred is N-[3-alkyl(12,14)oxy-2-hydroxypropyl]-L-arginine hydrochloride (manufactured by Ajinomoto Co., Inc., tradename "Aminosafe LKA-60").

Further, a disinfectant having a disinfection or preservative effect may be added to the solution for contact lenses of the present invention so as to advantageously obtain an effect of sterilizing contact lenses. As such a disinfectant, a proper one may be selected from known disinfectants, and used alone or in combination as a mixture of at least two. Preferably, an organic nitrogen type disinfectant having an excellent disinfection or preservative effect is advantageously used, and among the organic nitrogen type disinfectants, particularly recommended is a quaternary ammonium compound or its polymer, or a biguanide compound or its salt or its polymer.

Here, the quaternary ammonium compound or its polymer may, for example, be an alkylammonium salt such as a tetraalkylammonium salt such as alkyltrimethylammonium chloride or a trialkylbenzylammonium salt such as octadecyldimethylbenzylammonium chloride; an alkylhydroxyalkylimidazoline quaternary salt represented by hydroxyethylalkylimidazoline chloride; an alkylisoquinolium salt represented by alkylisoquinolium bromide; an alkylpyridinium salt; a cationic surfactant such as an amideamine, a polycationic one such as a condensate of a diamine and a dihalogen compound as disclosed in Japanese Patent No. 2550036, or halogenated benzalconium. Further, the biguanide compound or its salt or its polymer may, for example, be polyhexamethylene biguanide or chlorhexidine.

Further, in the present invention, a thickener may be added so as to properly adjust the viscosity of the solution for contact lenses, and a nonionic or cationic thickener such as a gum such as a heteropolysaccharide; a synthetic organic high-molecular compound such as polyvinyl alcohol, poly-N-vinyl pyrrolidone, polyethylene glycol, polypropylene glycol or polyacrylamide; a cellulose derivative such as hydroxyethyl cellulose, hydroxypropyl methyl cellulose, carboxymethyl cellulose or methyl cellulose; or a starch derivative, may be used.

Further, with respect to the solution for contact lenses of the present invention, if the pH value or the osmotic pressure is too high or too small, there is a fear that the eye may be irritated or eye problems may be caused, and accordingly the pH value of the solution is preferably adjusted within a range of from about 5.3 to about 8.5 by addition of a pH adjustor, and the osmotic pressure is preferably adjusted within a range of from about 200 to about 400 mOsm/kg by addition of an isotonicity agent. As the pH adjustor to be used for adjustment of pH, e.g. sodium hydroxide or hydrochloric acid may be used, and as the isotonicity agent to be used for adjustment of the osmotic pressure, at least one compound selected from the group consisting of saccharides, sugar alcohols, and polyhydric alcohols and their ethers and esters, is usually used.

In order to keep the pH of the solution for contact lenses within the above effective and ophthalmologically safe range, usually at least one buffering agent may be added. As the buffering agent, a conventionally known one may optionally be selected and used. Specifically, acids such as phosphoric acid, boric acid and oxycarboxylic acid, salts thereof (such as sodium salt), and further, Good-Buffer, tris(hydroxymethyl)aminomethane (Tris) and bis(2-hydroxyethyl)iminotris(hydroxymethyl)methane (Bis-Tris), may, for example, be mentioned from the viewpoint that they have safety for the eye and influences over a contact lens can be minimized.

Further, there is a possibility that e.g. calcium as a stain from the tear may be deposited or adsorbed on a contact lens, particularly on a soft contact lens in general, and accordingly a chelating agent may advantageously be added to the solution for contact lenses to prevent such inconvenience. As the chelating agent, ethylenediaminetetraacetic acid (EDTA) or its salt, such as disodium ethylenediamine tetraacetate (EDTA·2Na) or trisodium ethylenediamine tetraacetate (EDTA·3Na), may, for example, be used.

As evident from the above explanation, as the aqueous medium to which the above amino acid type cationic surfactant and nonionic surfactant and another component are added to prepare the solution for contact lenses of the present invention, in addition to water itself such as running water, purified water or distilled water, physiological saline or a sodium chloride-containing aqueous solution, or a known solution for contact lenses, may, for example, be employed so long as it is a solution consisting essentially of water.

When a contact lens is cleaned by using the solution for contact lenses of the present invention thus obtained, an optional means may be employed, such as a means of soaking a contact lens taken off from the eye in the solution for contact lenses of the present invention filled in a proper container for a predetermined time, or cleaning a contact lens with said solution by rubbing and then soaking the lens in the solution for contact lenses of the present invention filled in a proper container for a predetermined time, or a means of using said solution for contact lenses of the present invention as eye drops and administering them to the eye having a contact lens put thereon so that the contact lens is brought into contact with the solution for contact lenses on the eye and is cleaned.

Accordingly, when a contact lens is cleaned by the solution for contact lenses of the present invention, a stain due to the tear such as lipids attached to the contact lens can effectively be removed. Further, as the solution for contact lenses of the present invention has a high safety for the eye, no eye problems or the like will be caused even when the cleaning treatment of a contact lens by soaking or rubbing is carried out for a long period of time. Further, the amino acid type cationic surfactant has disinfection power in addition to the cleaning power, whereby a sterilization treatment of a contact lens can effectively be carried out in addition to the cleaning treatment of the contact lens.

Further, a contact lens to which the solution for contact lenses of the present invention is applied is not particularly limited, and the solution for contact lenses applies to all types of soft contact lenses including a low water-absorptive type and a high water-absorptive type, and hard contact lenses, and e.g. the material of a contact lens is not limited.

Now, the present invention will be explained in further detail with reference to Examples and Comparative Examples. However, it should be understood that the present invention is by no means restricted to such specific Examples. Further, various changes, modifications or improvements may be made to the present invention other than the following Examples or the above specific description by those skilled in the art without departing from the scope of the present invention.

Test on Cleaning Effect Over Lipids

The cleaning effect of the solution for contact lenses of the present invention over lipids was examined by means of a lipid-solubilizing rate method. Specifically, predetermined additive components were added to purified water in various proportions as identified in the following Table 1 to prepare various sample solutions having a pH of 7.3 (Examples 1 and 2 and Comparative Examples 1 to 10) firstly.

For the preparation of sample solutions, among additive components of the solution for contact lenses of the present invention, as surfactants, N-coconut oil fatty acid acyl L-arginine ethyl·DL-pyrrolidone carboxylate (CAE) as an amino acid type cationic surfactant, Poloxamer 407 (Px407) which is a polyoxyethylene-polyoxypropylene block copolymer as a nonionic surfactant, and N-[3-alkyl(12,14) oxy-2-hydroxypropyl]-L-arginine hydrochloride (LMA-60, manufactured by Ajinomoto Co., Inc.) as an ampholytic surfactant were used. Further, for the preparation of sample solutions for contact lenses of Comparative Examples, as the surfactant which is one of addition components, in addition to the above-mentioned CAE or Px407, sodium N-lauroylmethyltaurine (LMT, anionic surfactant), trimethylglycine (Aquadew, ampholytic surfactant), decaglyceryl monooleate (Decaglyn, nonionic surfactant) or polyoxyethylene(30)polyoxypropylene(6)decyltetradecyl ether (PEN, nonionic surfactant) was used. Further, as other additive components, hydroxypropylmethyl cellulose (HPMC) as a thickener, dihydrate of disodium ethylenediaminetetraacetate (EDTA·2Na·2H$_2$O) as a chelating agent, bis(2-hydroxyethyl)iminotris(hydroxymethyl)methane(Bis-Tris) as a buffering agent and sodium chloride (NaCl) were used. Further, for adjustment of pH, sodium hydroxide was used.

Then, using a colored lipid obtained by mixing triglyceride as a lipid and Sudan I as a pigment in a weight ratio of 99:1, 0.5 g thereof was accommodated in a predetermined test bottle, 20 mL of the above obtained sample solution was further added and accommodated in the test bottle, and the opening of the test bottle was covered with a proper lid. This operation was carried out with respect to each of the above sample solutions.

Further, each test bottle having the colored lipid and the sample solution accommodated therein thus prepared, was shaken at a temperature of 25° C. for 24 hours at a constant rate and further left to stand for a predetermined time, and a supernatant fluid in each test bottle was collected, and the absorbance at 485.5 nm was measured with respect to each supernatant fluid by means of a spectrophotometer (recording spectrophotometer UV-2200, manufactured by Shimadzu Corporation).

From the values of the absorbance thus measured, the is ratio (relative value) of the absorbance of each sample solution to the absorbance of the sample solution of Comparative Example 2 was obtained, and the results are shown in the following Table 1 and in FIG. 1 as a bar graph. A value of the absorbance ratio higher than the absorbance ratio in Comparative Example 2 (=1) i.e. a relatively high absorbance indicates an excellent cleaning effect over lipids, specifically excellent lipid-solubilizing power.

TABLE 1

| Additive components | Examples | | Comparative Examples | | | | | | | | | |
|---|---|---|---|---|---|---|---|---|---|---|---|---|
| | 1 | 2 | 1 | 2 | 3 | 4 | 5 | 6 | 7 | 8 | 9 | 10 |
| CAE | 0.1 | 0.1 | 0.1 | — | — | — | — | — | — | — | — | — |
| Px407 | 0.5 | 0.5 | — | 0.5 | — | — | — | — | 0.5 | 0.5 | 0.5 | 0.5 |
| LMA-60 | — | 0.1 | — | — | — | — | — | — | — | — | — | — |
| LMT | — | — | — | — | 0.1 | — | — | — | 0.1 | — | — | — |
| Aquadew | — | — | — | — | — | 0.1 | — | — | — | 0.1 | — | — |
| Decaglyn | — | — | — | — | — | — | 0.1 | — | — | — | 0.1 | — |
| PEN | — | — | — | — | — | — | — | 0.1 | — | — | — | 0.1 |
| HPMC | 0.275 | 0.275 | 0.275 | 0.275 | 0.275 | 0.275 | 0.275 | 0.275 | 0.275 | 0.275 | 0.275 | 0.275 |
| EDTA.2 Na.2 H$_2$O | 0.05 | 0.05 | 0.05 | 0.05 | 0.05 | 0.05 | 0.05 | 0.05 | 0.05 | 0.05 | 0.05 | 0.05 |
| Bis-Tris | 0.1 | 0.1 | 0.1 | 0.1 | 0.1 | 0.1 | 0.1 | 0.1 | 0.1 | 0.1 | 0.1 | 0.1 |
| NaCl | 0.87 | 0.87 | 0.87 | 0.87 | 0.87 | 0.87 | 0.87 | 0.87 | 0.87 | 0.87 | 0.87 | 0.87 |
| Absorbance ratio | 21.71 | 16.37 | 0.19 | 1 | 0.06 | 0.25 | 2.48 | 12.9 | 12.36 | 0.92 | 6.76 | 14.01 |

Additive proportion (unit): w/v %

As evident from the results shown in Table 1 and FIG. 1, it was confirmed that each of the sample solutions of Examples 1 and 2 showed high lipid-solubilizing power as compared with the sample solutions of Comparative Examples 1 to 6 wherein a single surfactant alone was used as the surfactant to be a cleaning component. Further, it was confirmed that the sample solutions of Examples 1 and 2 showed high lipid-solubilizing power as compared with the sample solutions of Comparative Examples 7 to 10 wherein a surfactant other than the amino acid type cationic surfactant and Poloxamer 407 which is a nonionic surfactant were used together. From these findings, it is estimated that the lipid-solubilizing powers of the amino acid type cationic surfactant and the nonionic surfactant can synergistically be increased by combining and incorporating them in a solvent.

Test on Adjustability to Lenses

To examine the adjustability of the solution for contact lenses of the present invention to contact lenses, the following test was carried out. Namely, in the same manner as in the above test on cleaning effect over lipids, predetermined additive components were added to purified water in proportions as identified in the following Table 2, to prepare various sample solutions having a pH of 7.3 (Examples 3 and 4 and Comparative Example 11).

On the other hand, a plurality of commercially available soft contact lenses (Menicon Soft 72, manufactured by Menicon Co., Ltd., lens diameter: 13.5 mm) were prepared, and such lenses were soaked in physiological saline kept at a temperature of 25° C., and the lens diameters of the contact lenses in a soaked state were measured by means of a projector (universal projector manufactured by Nikon Corporation), and the obtained measured values were recorded as initial values of the lens diameters.

Then, the contact lenses of which the initial values of the lens diameters were thus obtained were soaked in the sample solution prepared as mentioned above at a temperature of 25° C. for 3 days, and the lens diameters were measured in a soaked state by means of the same projector as mentioned above. This operation was carried out by using three contact lenses with respect to each sample solution.

Then, the difference (d) between the measured value of the lens diameter thus obtained (value after the soaking) and the initial value of the lens diameter was obtained in accordance with the following formula:

d=(value after the soaking)−(initial value)

with respect to each contact lens, and the average value of the obtained values was obtained with respect to each sample solution. The results are shown in the following Table 2 as the change in lens diameter. Needless to say, the smaller the value of the change in lens diameter, the more excellent the adjustability to contact lenses, and further, the value of the change in lens diameter is particularly preferably within ±0.2 mm.

TABLE 2

| Additive | Examples | | Comparative Example |
|---|---|---|---|
| components | 3 | 4 | 11 |
| CAE | 0.05 | 0.1 | — |
| Px407 | 0.5 | 0.5 | 0.5 |
| HPMC | 0.275 | 0.275 | 0.275 |
| EDTA · 2Na · 2H$_2$O | 0.05 | 0.05 | 0.05 |
| Bis-Tris | 0.1 | 0.1 | 0.1 |
| NaCl | 0.87 | 0.87 | 0.87 |

TABLE 2-continued

| Additive | Examples | | Comparative Example |
|---|---|---|---|
| components | 3 | 4 | 11 |
| Change in lens diameter (mm) | 0.027 | 0.012 | 0.023 |

Addition proportion (unit): w/v %

As evident from the results shown in the above Table 2, it was confirmed that each of the sample solutions of Examples 3 and 4 had no influence over the shape (diameter) of contact lenses at an equal level to the sample solution of Comparative Example 11 i.e. a conventional sample solution wherein Poloxamer 407 alone was used and no CAE was used together. Accordingly, it is understood that the solutions of the present invention are advantageous in view of the adjustability to contact lenses.

Test on Sterilization Effect

In order to examine the sterilization effect of the solution for contact lenses of the present invention over fungi, the following test was carried out. Namely, in the same manner as the above test on cleaning effect over lipids and the test on adjustability to lenses, predetermined additive components were added to purified water in proportions as identified in the following Table 3 to prepare various sample solutions having a pH of 7.3 (Examples 5 and 6 and Comparative Example 12).

As one of test fungi, Candida albicans, IFO 1594) was selected and cultured on a Sabouraud's glucose agar medium manufactured by Nihon Pharmaceutical Co., Ltd. at 32° C. for 18 hours, and using this cultured fungus, a suspension was prepared so that the number of bacteria was from $10^7$ to $10^8$ cfu/ml, and 100 μl thereof was added to 10 ml of each of sample solutions of Examples 5 and 6 and Comparative Example 12. Then, the sample solutions of Examples 5 and 6 and Comparative Example 12 having the suspension added thereto were incubated at room temperature for 6 hours, and the number of surviving bacteria (cfu) was counted by a pour plate culture method. Here, in the pour plate culture method, the Sabouraud's glucose agar medium was used as a culture medium, and the culture was carried out at 32° C. for 3 days.

Further, as another test fungus, Staphylococcus aureus, IFO 13276) was selected and cultured on "SCD agar medium", tradename, manufactured by Nihon Pharmaceutical Co., Ltd. at 32° C. for 18 hours, and using this cultured fungus, a suspension was prepared so that the number of bacteria was from $10^7$ to $10^8$ cfu/ml, and 100 μl thereof was added to 10 ml of each of the sample solutions of Examples 5 and 6 and Comparative Example 12. Then, the sample solutions of Examples 5 and 6 and Comparative Example 12 having the suspension added thereto were incubated at room temperature for 20 minutes, and the number of surviving bacteria was counted by a pour plate culture method. Here, in the pour plate culture method, the above SCD agar medium was used as a culture medium, and the culture was carried out at 32° C. for 3 days.

After the numbers of surviving bacteria of the test fungi were measured, the logarithmic decrements of the respective fungi were calculated in accordance with the following formula, and the results are shown in the following Table 3.

Logarithmic decrement=log(number of inoculated bacteria)−log(number of surviving bacteria)

TABLE 3

| | Examples | | Comparative Example |
|---|---|---|---|
| | 5 | 6 | 12 |
| Additive components | | | |
| CAE | 0.02 | 0.005 | — |
| Px407 | 0.50 | 0.50 | 0.50 |
| HPMC | 0.275 | 0.275 | 0.275 |
| EDTA · 2Na · 2H$_2$O | 0.05 | 0.05 | 0.05 |
| Bis-Tris | 0.10 | 0.10 | 0.10 |
| NaCl | 0.87 | 0.87 | 0.87 |
| Logarithmic decrement | | | |
| *Candida albicans* | | | |
| After 15 min. | 0.78 | 0.00 | 0.00 |
| After 60 min. | 1.00 | 0.40 | 0.40 |
| After 240 min. | 3.16 | 1.00 | — |
| *Staphylococcus aureus* | | | |
| After 15 min. | >4.05 | 0.33 | — |
| After 60 min. | >4.05 | 0.64 | 0.35 |
| After 240 min. | >4.05 | >4.05 | — |

Addition proportion (unit): w/v %

In the above Table 3, with respect to the logarithmic decrement in the case where *Candida albicans* was used as the test fungus, in Comparative Example 12, the logarithmic decrement was only 0.40 60 minutes after inoculation of the fungus, whereas in Examples 5 and 6, the logarithmic decrement was equal to or higher than that of Comparative Example 12 60 minutes after inoculation of the fungus. Likewise, with respect to the logarithmic decrement in the case where *Staphylococcus aureus* was used as the test fungus, in Comparative Example 12, the logarithmic decrement was only 0.35 60 minutes after inoculation of the fungus, whereas in Examples 6, the logarithmic decrement was 0.64 60 minutes after inoculation of the fungus, and in Example 5, the logarithmic decrement was higher than 4.05 only 15 minutes after inoculation of the fungus, and it was higher than 4.05 60 minutes and 240 minutes after. From these results, it is understood that the solution for contact lenses of the present invention is advantageous also in view of a sterilization treatment of contact lenses.

As evident from the above explanation, the solution for contact lenses of the present invention comprises an amino acid type cationic surfactant and at least one nonionic surfactant, whereby cleaning powers of the amino acid type cationic surfactant and the nonionic surfactant can synergistically be increased, and accordingly an excellent cleaning effect over a stain of lipids on a contact lens, a high safety for the eye, and in addition, a sterilization effect which the amino acid type cationic surfactant originally possesses, can advantageously be realized.

What is claimed is:

1. A solution for contact lenses which comprises a cationic surfactant consisting essentially of from 0.001 to 1.0% (w/v) of N-coconut oil fatty acid acyl L-arginine ethyl DL-pyrrolidone carboxylate, and from 0.1 to 3.0% (w/v) of at least one nonionic surfactant.

2. The solution for contact lenses according to claim 1, wherein the nonionic surfactant is a polyoxyethylene-polyoxypropylene block copolymer or its derivative.

3. The solution for contact lenses according to claim 1, further comprising at least one ampholytic surfactant.

4. The solution for contact lenses according to claim 1, further comprising at least one member selected from the group consisting of a disinfectant, a thickener, a buffering agent, a chelating agent, an isotonicity agent and a cationic surfactant other than the cationic surfactant consisting essentially of an amino acid derivative and an anionic surfactant.

5. A method for cleaning a contact lens, comprising:

contacting said contact lens with the solution according to claim 1.

* * * * *

UNITED STATES PATENT AND TRADEMARK OFFICE
CERTIFICATE OF CORRECTION

PATENT NO.    : 6,417,144 B2
DATED         : July 9, 2002
INVENTOR(S)   : Tsuzuki et al.

It is certified that error appears in the above-identified patent and that said Letters Patent is hereby corrected as shown below:

<u>Title page,</u>
Item [73], Assignee, the information is incorrect. It should read
-- [73]  Assignee:  Menicon Co., Ltd., Nagoya (JP) --

Signed and Sealed this

Eighteenth Day of March, 2003

JAMES E. ROGAN
*Director of the United States Patent and Trademark Office*